May 25, 1965 O. O. DUNHAM Plant Pat. 2,518
CHRYSANTHEMUM PLANT
Filed March 4, 1964
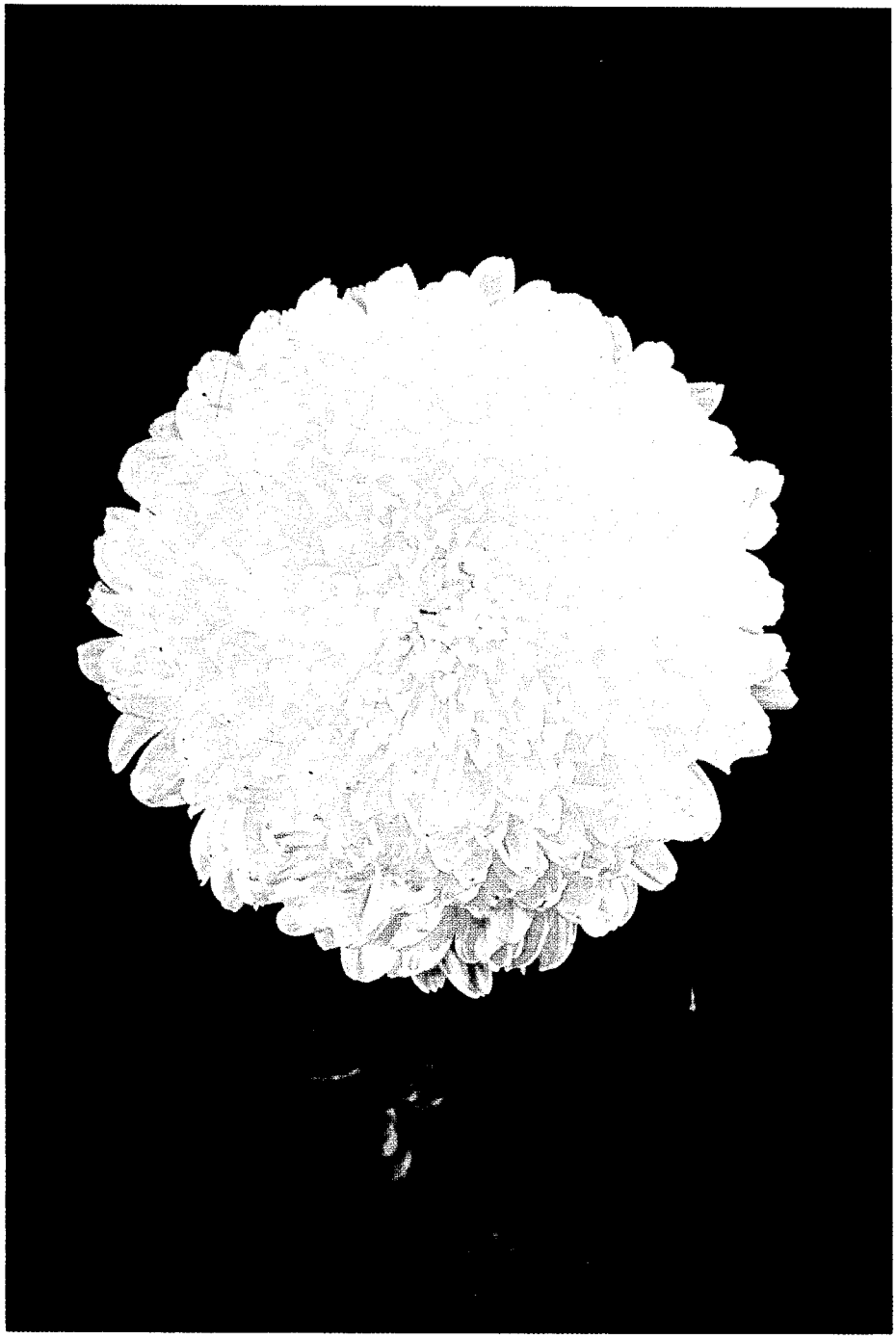
Inventor
O. O. Dunham
by Robb & Robb
attorneys United States Patent Office Plant Pat. 2,518
Patented May 25, 1965

2,518
CHRYSANTHEMUM PLANT

Orville O. Dunham, Niles, Mich., assignor to Stern's Nurseries, Inc., Geneva, N.Y., a corporation of New York Filed Mar. 4, 1964, Ser. No. 349,515
1 Claim. (Cl. Plt.—77)

This invention relates to a new variety of chrysanthemum plant which I have found distinctive and which is the result of an intensive program of breeding, cross-breeding and hybridization in general, from which I periodically select plants which have desirable characteristics, having initially selected the parents thereof in order to attempt to develop the desirable characteristics heretofore found of value in the chrysanthemum art.

My present variety of chrysanthemum plant is one which has taken some of the characteristics of the parents and availed of the desirable ones, the undesirable or less desirable characteristics at any rate, having been improved upon hereby.

My present invention relates to a variety of chrysanthemum plant which is the result of cross-breeding the plant disclosed in Plant Patent No. 2,005 ("Full Moon"), with another variety of my own origination which I designate as "Freedom" and which is unpatented.

The instant variety is one which has availed of the earliness to bloom of the variety disclosed in Plant Patent No. 2,005, the latter being the seed parent, other characteristics of this particular variety likewise being passed on to the variety of this invention, including the generally large, creamy white, incurving, ball-shaped bloom, which is very large in diameter and a relatively deep form, and growing on upright stems 20 to 24 inches in height.

The variety "Freedom," is a deeply reflexing variety, of pure white and somewhat smaller diameter than the variety of Plant Patent No. 2,005, the "Freedom" variety having extremely double petalage, well rounded petals, although the plant itself is only of medium height and compact. This variety "Freedom" likewise blooms later than the variety of Plant Patent No. 2,005 but in any event is found on strong, straight, upright stems, a characteristic passed on to the variety of this invention.

The variety of the instant invention has rich creamy colored blooms of 6 to 7 inch diameter on extremely stiff, straight, tall stems, each bloom having a fully incurving center with deeply reflexing outer petals.

The instant variety produces symmetrical blooms of quite uniformly desirable shape which makes an excellent show plant in any event.

The result of the hybridization previously referred to and described in detail, has been to produce my present new and distinct variety of chrysanthemum characterized by the rich creamy white color of its blooms which have a suggestion of Brilliant Greenish-Yellow at their centers, the very large size of the blooms with full incurving centers and deeply reflexing outer petals likewise being distinctive, the tall, long, straight stems, very double petalage and earliness to bloom being other characteristics which I have endeavored to produce and been successful in so doing in this particular variety.

As grown in the vicinity of Niles, Michigan, in uniform culture, plants of my new variety grow taller than either of the parents on the average, and particularly of parent "Freedom," my new variety growing commonly to a height of 24 inches.

As will be understood from the foregoing, my new variety derives a number of characteristics from both parents but the desirable characteristics which are present in the instant variety to make a show plant, have been emphasized hereby.

Under the conditions of culture previously mentioned, which have been carried out in the region of Niles, Michigan, plants of my new variety have good foliage, to support the very large diameter blooms which often grow to a size of 6 to 7 inches in diameter.

My new variety has been asexually reproduced by cuttings in the vicinity of Niles, Michigan, observations made herein and noted hereafter as a basis for this description, having been made in mid-October.

My new variety has been found to retain its distinctive characteristics through successive asexual reproduction.

In the accompanying drawing, my new variety is disclosed in the form of a bloom, of typical form and in a color illustration which is as reasonably accurate as is possible with perhaps some slight overemphasis on the Brilliant Greenish-Yellow center which, in the actual bloom, appears more of a creamy general tonality from a distance.

The following is a detailed description of my new variety of chrysanthemum plant, the color references being to the Nickerson Color Fan published by the Munsell Color Company:

*Description*

Parentage: Seedling.
- *Seed parent.*—Plant Patent No. 2005.
- *Pollen parent.*—"Freedom" (unpatented).

Classification: Botanic—*Chrysanthemum indicum.*

*Flower*

Blooming Habit: Blooms profusely and continuously from early in the season, until late in the season or a killing frost.

Bud:
- *Size.*—Large.
- *Form.*—Short with flat top.
- Not affected by hot or wet weather to any material extent.

Color:
- *When sepals first divide.*—Greenish-white.
- *When petals begin to unfurl.*—Greenish-creamy white.
- *When half blown.*—Inside of petals—creamy white. Reverse of petals—creamy white.
- *Sepals.*—Of no consequence.
- *Calyx.*—Shape—funnel. Size—large. Aspect—hairy.
- *Peduncle.*—Length—medium. Aspect—rough. Strength—stiff and erect. Bud opens well and is not affected by hot or wet weather.

Bloom:
- *Size.*—Very large.
- *Average size when fully expanded.*—6 to 7 inches.
- *Borne.*—In clusters, rounded.
- *Stems.*—Long and strong.
- *Form.*—Globular.
- *Permanence.*—Retains its form to the end.
- *Petalage.*—Very double with innumerable petals under normal conditions.

Color:
- *Center of flower.*—Creamy white with suggestion of brillant greenish-yellow—7.5Y9/8.
- *Outer petals.*—White.
- *Base of petals.*—Greenish-white.
- *Inside of petals.*—Creamy white.
- *Reverse of petals.*—White.
- *General tonality from a distance.*—Creamy white with suggestion of Brilliant Greenish-yellow—7.5Y 9/8.
- *Discoloration.*—Generaly tonality at end of: First week—retains same as when first open. Second week—retains same as above. Third week—also retains same as above.

Petals:

*Texture.*—Thick and soft. Not affected by hot or wet weather.

*Appearance.*—Inside—satiny. Outside—satiny.

*Form.*—Pointed.

*Arrangement.*—Irregular.

*Persistence.*—Hang on and dry.

*Lastingness.*—On the plant—very long. As cut flower—very long.

Genital organs:

*Stamens, anthers.*—Medium and few.

*Arrangement.*—Regular around styles.

*Stamens, filaments.*—Medium.

*Styles.*—Columnar.

*Length.*—Medium.

*Ovaries.*—All enclosed in calyx.

Plant:

*Form.*—Bush.

*Growth.*—Very vigorous, upright and branching.

Foliage:

*Size.*—Very large.

*Quantity.*—Abundant.

*Texture.*—Upper side—smooth. Under side—rough.

*Ribs and veins.*—Ordinary.

*Edge.*—Serrated.

*Serration.*—Single.

I claim:

A new and distinct variety of chrysanthemum plant substantially as herein disclosed, characterized as to novelty by the rich creamy white color of its blooms having a suggestion of Brilliant Greenish-Yellow at their centers, the very large size of the blooms, with full incurving centers and deeply reflexing outer petals, the blooms being very symmetrical, tall, long, straight stems, the very double petalage, and earliness to bloom.

No references cited.

ABRAHAM G. STONE, *Primary Examiner.*